United States Patent [19]

McGowan

[11] Patent Number: 5,118,613

[45] Date of Patent: Jun. 2, 1992

[54] DETERMINATION OF HDL WHOLE BLOOD

[75] Inventor: Michael W. McGowan, Mundelein, Ill.

[73] Assignee: Abbott Laboratories, Abbott Park, Ill.

[21] Appl. No.: 438,656

[22] Filed: Nov. 17, 1989

[51] Int. Cl.$^5$ ............... G01N 33/92; G01N 21/31; G01N 21/77; G01N 33/49

[52] U.S. Cl. ............... 435/11; 436/71; 436/86; 436/87; 436/177; 436/179

[58] Field of Search ............... 436/60,71, 164, 171, 436/177, 56, 175, 18, 179, 86, 87; 435/11, 23

[56] References Cited

U.S. PATENT DOCUMENTS 4,699,887 10/1987 Abbott et al. ............... 436/70
4,772,561 9/1988 Genshaw ............... 436/169

OTHER PUBLICATIONS

N. Tietz, Saunders, "Methods For The Determination of Lipids and Lipoproteins" Textbook Of Clinical Chemistry, 876-881 (1986).

Bentzen et al., "Direct Determination of Lipoprotein Cholesterol Distribution With Micro-Scale Affinity Chromatrography Columns", Clinical Chemistry, vol. 28, No. 7, 1451-1456 (1982).

Lippi et al., "Determination of High Density Lipoprotein Cholesterol In Venous And Capillary Whole Blood", Journal Of Lipid Research, vol. 29, 112-115 (1988).

Abbott Laboratories, Abbott Park, Illinois, Product Literature, "Vision ® Whole Blood HDL Cholesterol" Pamphlet No. 3A21.

Burstein et al. "Rapid Method For The Isolation of Lipoproteins From Human Serum By Precipitation With Polyanions", Journal Of Lipid Research, vol. 11, 583-59 (1970).

Finley et al., "Cholesterol in High-Density Lipoprotein: Use of Mg$^{2+}$/Dextran Sulfate In Its Enzymatic Measurement" Clinical Chemistry, vol. 24, No. 6, 931-933 (1978).

C. Allain et al., "Enzymatic Determination of Total Serum Cholesterol", Clinical Chemistry, vol. 20, No. 4, 470-476 (1974).

Artiss et al., "A Sensitive Reaction for Dilute Cholesterol Determinations", Michrochemical Journal, 25, 535-542 (1980).

Primary Examiner—David L. Lacey
Assistant Examiner—Daniel Redding
Attorney, Agent, or Firm—Richard D. Schmidt

[57] ABSTRACT

A method for separating HDL from whole blood anticoagulated with EDTA is disclosed. The method includes, as a first step, mixing the anticoagulated whole blood with an aqueous solution composed of magnesium ++ cations and dextran sulfate 500 in such proportions and of such concentration (a) that substantially all of the LDL and VLDL lipoproteins and substantially all of the chylomicrons are precipitated while (b) substantially all of the HDL remains in solution.

The method also includes the step of sedimenting the precipitated lipoproteins, the chylomicrons and the red blood cells by centrifuging, which can be low gravity centrifuging, and can include the step of determining the cholesterol, triglyceride, phospholipid or protein content of the supernatant. Also disclosed is a method wherein the reagent additionally contains a colored species which can be used to determine dilution of the supernatant, and which includes the additional steps of determining the dilution of the supernatant and the dilution factor, and multiplying the value determined for cholesterol, triglyceride, phospholipid or protein content of the supernatant times the dilution factor to determine the corresponding content of the blood sample.

5 Claims, No Drawings

DETERMINATION OF HDL WHOLE BLOOD

FIELD OF THE INVENTION

This invention relates to a method for separating HDL (high density lipoprotein) from whole blood and the determination of the cholesterol, triglyceride, phospholipid or protein content HDL of the whole blood sample.

BACKGROUND OF THE INVENTION

Ultracentrifugation is the reference method for separating lipoproteins from plasma, although other methods have also been reported, e.g., electrophoretic methods which depend on their differing surface charges and molecular sizes, precipitation methods where insoluble complexes are formed with polyanions and divalent cations, gel or membrane filtration methods which separate on the basis of molecular size, and isolation methods using antibodies to apolipoproteins. Three different ultracentrifugation operations are required to effect the separation:

(1) 16 hours at a plasma density of 1.006 grams per milliliter and 10,000 × gravity, followed by recovery of VLDL by a technique called tube-slicing;

(2) 20 hours at a plasma density of 1.063 grams per milliliter and 10,000 × gravity followed by a density adjustment and recovery of HDL; and (3) at a plasma density of 1.210 grams per milliliter to recover HDL.

The isolated lipoprotein fractions are then quantitatively recovered, reconstituted to the original volume of the plasma aliquot, and quantitated by measurement of their cholesterol, triglyceride, phospholipid or protein content (*Textbook of Clinical Chemistry*, Tietz, Saunders, 1986, page 876).

Various precipitation techniques are recommended for the determination of HDL-Cholesterol in small volumes of plasma although, again, ultracentrifugation is the reference method. The precipitation methods use divalent cations and sulfated polysaccharides or sodium phosphotungstate to precipitate all of the lipoproteins except HDL. Centrifugation can then be used to remove the precipitated lipoproteins, after which HDL remaining in the supernatant can be quantitated by its cholesterol content. Examples of precipitating reagents include:

heparin—$Mn^{++}$
dextran sulfate 500—$Mg^{++}$
sodium phosphotungstate—$Mg^{++}$
heparin—$Ca^{++}$ and
concanavalin A—polyethylene glycol 6000.
(ibid., page 879)

The use of affinity column chromatography to isolate α and β lipoprotein fractions from serum and plasma has been described (*Clinical Chemistry*, Volume 28, No. 7, pages 51 et seq., 1982; see, also, a system that has been offered under the trade designations LDL-Direct and LDL-Direct Plus). A polypropylene column equipped with porous polyethylene filter discs and packed with a heparin-agarose affinity medium was used to produce an α-lipoprotein fraction (which contains all the lipoproteins that do not specifically bind to the column—said to be essentially the non-atherogenic components, similar to the HDLs obtained by ultracentrifugation) and a β-lipoprotein fraction. The β-fraction, which is ultimately desorbed from the column with saline, is said to be essentially the LDL (low density lipoprotein) and VLDL (very low density lipoprotein) fractions obtained by ultracentrifugation. The α- and β-fractions were then analyzed for cholesterol or the like and the β-:α-lipoprotein cholesterol ratio was determined. This ratio, it is said, may better indicate a patient's risk of stroke or coronary heart disease than the value for HDL cholesterol alone.

It has also been reported ("Determination of high density lipoprotein cholesterol in venous and capillary whole blood", Lippi, U. et al., *Journal of Lipid Research*, Volume 29, 1988, pages 112 et seq.) that HDL Cholesterol can be determined in whole blood anticoagulated with EDTA, using a precipitation mixture containing 99.9 grams per liter of polyethylene glycol 6000, 37.4 milligrams per liter of dextran sulfate and 2.6 millimoles per liter of $MgCl_2$. The procedure is described as involving separating HDL from plasma or whole blood by adding 25 microliters of plasma or 50 microliters of whole blood to 250 microliters of the precititation mixture, gentle mixing for a few seconds, incubating for 10 minutes and centrifuging at 1,500 × gravity for 10 minutes and determination of HDL Cholesterol by adding 200 microliters of supernatant to 1.0 milliliter of the enzymatic cholesterol reagent and reading absorbances at 500 nanometers.

BRIEF DESCRIPTION OF THE INVENTION

The instant invention is based upon the discovery that a reagent which is a solution composed of magnesium sulfate, dextran sulfate 500, 3-(2-pyridyl)-5,6-diphenyl-1,2,4-triazine-p,p'-disulfonic acid and ferrous ammonium sulfate can be used to make reliable separations of an HDL fraction from whole blood obtained by venipuncture or fingerstick. The separation is effected by mixing a whole blood sample anticoagulated with EDTA to the reagent, precipitating LDL and VLDL lipoproteins and chylomicrons (all of which are precipitated by the reagent solution) and then centrifuging. It is an advantage of the method that low gravity centrifuging for about 2 minutes (approximately 500 to about 1000 × gravity) is adequate to effect this sedimenting. The HDL fraction, which remains in solution in the supernatant, can then be quantitated by analyzing for cholesterol, triglyceride, phospholipid or protein content by mixing and with an appropriate reagent. The 3-(2-pyridyl)-5,6-diphenyl-1,2,4-triazine-p,p'-disulfonic acid forms a complex with $iron^{++}$ ions which is a colored species used at a known absorbance; as a consequence, the dilution of the sample can be calculated from a measurement of its absorbance in the supernatant.

DESCRIPTION OF THE PREFERRED EMBODIMENTS

The invention will be more fully understood from the following examples, number 1 of which constitutes the best mode presently contemplated by the inventors, but they are presented solely for the purpose of illustration, and are not to be construed as limiting.

As used herein, and in the appended claims, the terms "percent" and "parts" refer to percent and parts by weight, unless otherwise indicated; g means gram or grams; mg means milligram or milligrams; ng means nanogram or nanograms; cm means centimeter or centimeters; mm means millimeter or millimeters; l means liter or liters; μl means microliter or microliters; m/o means mole percent, and equals 100 times the number of moles of the constituent designated in a composition divided by the total number of moles in the composition; v/v means percent by volume; M means molar and equals the number of moles of a solute in 1 liter of a solution; N means normal, and equals the number of equivalents of a solute in 1 liter of solution; mM means millimoles; psi means pounds per square inch; and MPa means $10^6$ Pascals. All temperatures are in °C., unless otherwise indicated.

EXAMPLE 1

A 1000 µl microcentrifuge tube was charged with 250 µl reagent (as found in the Vision Whole Blood HDL Cholesterol test pack available from Abbott Laboratories) and 250 µl whole blood anticoagulated with 1.5 mg/ml of EDTA. The reagent contained 100 mM/l magnesium sulfate (added as the heptahydraate), 1.0 g/l dextran sulfate 500, 5.1 g/l 3-(2-pyridyl)-5,6-diphenyl-1,2,4-triazine-p,p'-disulfonic acid and 1.57 g/l ferrous ammonium sulfate. The reagent and the sample were mixed by shaking for about 10 seconds and an aliquot of the mixture was then centrifuged for 2 minutes at 500×gravity in bench-top centrifugal analyzer. The supernatant was added to an enzymatic cholesterol reagent and allowed to react and then the absorbance of the supernatant at two different wavelengths was determined. A computer comparison of the measured absorbances with computer stored data concerning previously determined absorbances of aqueous solutions of the reagent at known dilutions was determined and the dilution of the sample calculated. The bench-top centrifugal analyzer is commercially available from Abbott Laboratories, the assignee of the present invention, under the trade designation "Vision Analyzer". An enzymatic HDL Cholesterol determination was performed on the supernatant, and the determined value was multiplied by a dilution factor calculated from the previously determined dilution of the sample so that the product equaled the HDL Cholesterol content of the blood sample.

Test results on two different blood samples where the amount of blood mixed with the reagent was intentionally varied from 200 to 250 to 300 µl are set forth in the following table:

| HDL Cholesterol | Sample 1 Whole blood volume | | | Sample 2 Whole blood volume | | |
|---|---|---|---|---|---|---|
| | 200 µl | 250 µl | 300 µl | 200 µl | 250 µl | 300 µl |
| In supernatant | 11.81[1] | 14.2[2] | 16.0[3] | 21.3[4] | 25.9[5] | 29.8[6] |
| In blood | 38.6 | 39.9 | 41.4 | 67.1 | 71.2 | 72.4 |

[1] Dilution factor 3.27; 3.27 times 11.81 equals 38.6
[2] Dilution factor 2.81; 2.81 times 14.22 equals 39.9
[3] Dilution factor 2.59; 2.59 times 16.03 equals 41.4
[4] Dilution factor 3.15; 3.15 times 21.34 equals 67.1
[5] Dilution factor 2.75; 2.75 times 25.9 equals 71.2
[6] Dilution factor 2.43; 2.43 times 29.8 equals 72.4

EXAMPLE 2

The procedure described above in Example 1, sample size 250 µl, was used to determine HDL Cholesterol in eight different samples of whole blood; the results of these determinations are set forth in the following table, together with the results of HDL Cholesterol determinations on plasma recovered from each of the blood samples. The determinations of HDL Cholesterol in the plasma samples were made using a reagent composed of 91 mM/l magnesium sulfate and 0.9 g/l dextran sulfate 500. The HDL Cholesterol content of each of the samples is set forth below:

| Sample No. | HDL Cholesterol (in plasma) | HDL Cholesterol (in whole blood) |
|---|---|---|
| 1 | 50.4 | 49.2 |
| 2 | 47.5 | 43.6 |
| 3 | 45.5 | 47.3 |
| 4 | 45.6 | 44.6 |
| 5 | 30.5 | 29.6 |
| 6 | 89.1 | 93.6 |
| 7 | 66.2 | 70.7 |
| 8 | 42.7 | 41.4 |
| Average | 52.2 | 52.5 |

The foregoing results show that the determinations using whole blood gave values within 10 percent of those from the determinations using plasma, with no trend or significant bias. It will be appreciated that, if preferred, the triglyceride, phospholipid or protein content of the supernatant can be determined instead of the cholesterol content.

It has been found that the volume ratio of reagent to whole blood sample used in carrying out a determination according to the instant invention (1:1 in the foregoing procedures where the blood sample volume was 250 µl) is critical. For example, if this ratio is lowered substantially below 1:1 (i.e., by more than the 20 percent variation that is shown by the foregoing data to be acceptable), sedimentation of lipoproteins becomes poorer. The poorer sedimentation of lipoproteins can be offset, however, by suitable increases in the concentrations of the magnesium sulfate and of the dextran sulfate 500. Similarly, problems which occur if the ratio is increased above 1:1 can be offset by decreasing the concentrations of the magnesium sulfate and of the dextran sulfate 500 in the reagent. For example, if it is desired to use any given volume ratio of reagent to whole blood sample other than the nominal 1:1 ratio for which the procedure is described above, determinations can be made at that ratio and several different concentrations of magnesium$^{++}$ cations and dextran sulfate 500. By comparing the results of those determination with the results of a determination made by the procedure of Example 2, above, the required concentrations of magnesium$^{++}$ cations and of dextran sulfate 500 for that ratio can be selected readily.

So far as is known, the method is operable only when the reagent contains dextran sulfate 500 and $Mg^{++}$ cations in about the concentrations indicated above or in such other concentrations as may be required at different dilutions. The 3-(2-pyridyl)-5,6-diphenyl-1,2,4-triazine-p,p'-disulfonic acid and the ferrous ammonium sulfate present in such reagents, as disclosed above, impart a color which enables a determination of dilution, as described above. Other materials which impart a color in such a way as to enable a determination of dilution, so long as they do not interfere with the determination desired, can also be used.

While preferred embodiments of the invention have been disclosed, it will be appreciated that various changes and modification from the details specifically described are possible without departing from the spirit and scope of the following claims.

I claim:

1. A method for determining HDL cholesterol in whole blood anticoagulated with EDTA which comprises mixing the whole blood with an aqueous pretreatment reagent comprising magnesium$^{++}$ cations, dextran sulfate and an iron$^{++}$ complex with 3-(2-pyridyl)-5,6-diphenyl-1,2,4-triazine-p,p'-disulfonic acid, sedimenting the resultant precipitated lipoproteins, chylomicrons and the red blood cells by centrifugation at not more than about 1000×gravity for about 2 minutes, combining the resultant supernatant with a HDL cholesterol determination reagent and determining the dilution and the dilution factor of the supernatant, determining the quantitative value of the HDL cholesterol content of the supernatant and multiplying the determined quantitative value times the dilution factor to determine the HDL cholesterol content of the whole blood sample, wherein the magnesium$^{++}$ cations and dextran sulfate are present in such proportions and of such concentration that substantially all of the LDL and VLDL lipoproteins and substantially all of the chylomicrons are precipitated while substantially all of the HDL cholesterol remains in solution.

2. A method as claimed in claim 1 wherein substantially one volume of the blood sample is mixed with one volume of the aqueous pretreatment reagent.

3. A method as claimed in claim 1 wherein the centrifugation is conducted at from about 500×gravity to about 1000×gravity.

4. A method for determining HDL cholesterol, triglycerides, phospholipids or protein content of a whole blood sample anticoagulated with EDTA which comprises mixing the whole blood sample with an aqueous pretreatment comprising an iron$^{++}$ complex with 3-(2-pyridyl)-5,6-diphenyl-1,2,4-triazine-p,p'-disulfonic acid and magnesium$^{++}$ cations and dextran sulfate in such proportions and of such concentration that substantially all of the LDL and VLDL lipoproteins and chylomicrons are precipitated while substantially all of the HDL cholesterol remains in solution, centrifuging said sample and pretreatment reagent for at least about 2 minutes at from about 500×gravity to about 1000×gravity, combining the resultant supernatant with a determination reagent selected from the group consisting of HDL cholesterol, triglyceride, phospholipid and protein determining reagents and determining the dilution and dilution factor of the supernatant mixture, determining the quantitative value of the HDL cholesterol, triglyceride, phospholipid, or protein content of the supernatant mixture and multiplying the quantitative value times the dilution factor to determine the HDL cholesterol, triglyceride, phospholipid or protein content of the whole blood sample.

5. A method as claimed in claim 4 wherein the dilution and dilution factor are determined by absorption spectrophotometry.

* * * * *